United States Patent
Meglan

(10) Patent No.: US 12,106,508 B2
(45) Date of Patent: Oct. 1, 2024

(54) SYSTEMS AND METHODS FOR MITIGATING COLLISION OF A ROBOTIC SYSTEM

(71) Applicant: Covidien LP, Mansfield, MA (US)

(72) Inventor: Dwight Meglan, Westwood, MA (US)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 17/767,079

(22) PCT Filed: Nov. 18, 2020

(86) PCT No.: PCT/US2020/060987
§ 371 (c)(1),
(2) Date: Apr. 7, 2022

(87) PCT Pub. No.: WO2021/126447
PCT Pub. Date: Jun. 24, 2021

(65) Prior Publication Data
US 2022/0366594 A1   Nov. 17, 2022

Related U.S. Application Data

(60) Provisional application No. 62/950,372, filed on Dec. 19, 2019.

(51) Int. Cl.
*G06T 7/70* (2017.01)
*A61B 1/00* (2006.01)
(Continued)

(52) U.S. Cl.
CPC ............ *G06T 7/70* (2017.01); *A61B 1/00193* (2013.01); *A61B 34/20* (2016.02); *A61B 34/30* (2016.02);
(Continued)

(58) Field of Classification Search
CPC ............ G06T 7/70; G06T 2207/10012; G06T 2207/10068; G06T 2207/20081;
(Continued)

(56) References Cited

U.S. PATENT DOCUMENTS

| 10,022,192 B1 * | 7/2018 | Ummalaneni ......... B25J 9/1694 |
| 2008/0151041 A1 * | 6/2008 | Shafer .................... A61B 1/051 |
| | | 348/E13.001 |

(Continued)

OTHER PUBLICATIONS

International Search Report and Written Opinion of the International Searching Authority issued in corresponding application PCT/US2020/060987 mailed Mar. 4, 2021 (9 pages).

*Primary Examiner* — Dominic E Rego
(74) *Attorney, Agent, or Firm* — Carter, DeLuca & Farrell LLP

(57) ABSTRACT

Systems and methods are provided to mitigate potential collisions between a person and robotic system. In various embodiments, a robotic surgical system includes a robotic linkage including joints, an endoscope coupled to a distal portion of the robotic linkage and configured to capture stereoscopic images, and a controller in communication with the endoscope. The controller executes instructions to analyze the stereoscopic images from the endoscope to identify a human-held tool in the stereoscopic images and to estimate a type and/or pose of the human-held tool, infer a position of a person holding the human-held tool based on the type and/or pose of the human-held tool, determine a spatial relationship between the person and the robotic linkage based on the inferred position of the person, and generate a warning of potential collision between the person and the robotic linkage based on the determined spatial relationship.

20 Claims, 5 Drawing Sheets

(51) Int. Cl.
  *A61B 34/20* (2016.01)
  *A61B 34/30* (2016.01)
  *G06V 20/50* (2022.01)
  *A61B 17/00* (2006.01)
  *A61B 90/00* (2016.01)

(52) U.S. Cl.
  CPC .... *G06V 20/50* (2022.01); *A61B 2017/00119* (2013.01); *A61B 2034/2059* (2016.02); *A61B 2034/2065* (2016.02); *A61B 2034/301* (2016.02); *A61B 2090/067* (2016.02); *G06T 2207/10012* (2013.01); *G06T 2207/10068* (2013.01); *G06T 2207/20081* (2013.01); *G06T 2207/30004* (2013.01); *G06V 2201/034* (2022.01)

(58) Field of Classification Search
  CPC .......... G06T 2207/30004; A61B 34/20; A61B 34/30; A61B 1/00193; A61B 2034/2059; A61B 2034/301; A61B 2090/067; A61B 2017/00119; G06V 20/50; G06V 2201/034

See application file for complete search history.

(56) References Cited

U.S. PATENT DOCUMENTS

| | | |
|---|---|---|
| 2009/0192524 A1 | 7/2009 | Itkowitz et al. |
| 2010/0160929 A1* | 6/2010 | Rogers ................... A61B 34/30 606/130 |
| 2015/0202015 A1* | 7/2015 | Elhawary ............... A61B 90/06 606/130 |
| 2017/0172671 A1 | 6/2017 | Miller et al. |
| 2018/0279852 A1* | 10/2018 | Rafii-Tari ............... A61B 34/35 |
| 2018/0296281 A1* | 10/2018 | Yeung .................... A61B 34/32 |
| 2018/0325499 A1* | 11/2018 | Landey ............. A61B 1/00149 |
| 2019/0005848 A1 | 1/2019 | Garcia Kilroy et al. |
| 2019/0008595 A1 | 1/2019 | Popovic ................. A61B 34/20 |
| 2019/0159661 A1* | 5/2019 | Itkowitz .................. A61B 1/05 |
| 2020/0405411 A1* | 12/2020 | Draper ............. A61B 1/00149 |
| 2021/0128260 A1* | 5/2021 | Gonenc ............. A61B 17/3423 |

* cited by examiner

SYSTEMS AND METHODS FOR MITIGATING COLLISION OF A ROBOTIC SYSTEM

CROSS-REFERENCE TO RELATED APPLICATIONS

This application is a U.S. National Stage Application filed under 35 U.S.C. § 371(a) of International Patent Application No. PCT/US2020/060987, filed Nov. 18, 2020, which claims priority to and the benefit of, U.S. Provisional Application Ser. No. 62/950,372, filed on Dec. 19, 2019, the entire contents of which are incorporated by reference herein.

FIELD

The present technology generally relates to robotic surgical systems, and in particular, relates to systems and methods for mitigating collision of a robotic surgical system.

BACKGROUND

During surgical procedures, endoscopes have been used to visualize a surgical site. Particularly, in minimally invasive surgery including robotic surgery, stereoscopic image sensors have been used to allow a surgeon to visualize a surgical site.

A surgeon operating a robotic surgical system engages in a relatively small portion of organs inside of a patient and has a limited scope of view through a display, so the surgeon may not see the placement of persons assisting with the surgery. When a person is in close proximity to the robot arms, it is possible for the person to be contacted by or collide with an arm of the robotic system. Such collision can cause safety concerns. Therefore, there is continuing interest in developing and improving safety of robotic surgical systems.

SUMMARY

The techniques of this disclosure generally relate to mitigating or reducing potential collisions between a person and a robotic surgical system. As described in more detail herein, the type of a human-held tool and/or the pose/orientation of the human-held tool is the starting point for inferring the position of the person holding the human-held tool. Thus, the techniques disclosed herein for determining the position of a person holding a non-robotic tool is not based on an image of the person. The inferred position of the person is compared to the swept volume of the robotic surgical system to identify potential collisions.

In accordance with aspects of the disclosure, a robotic surgical system includes a robotic linkage including a plurality of joints, an endoscope coupled to a distal portion of the robotic linkage and configured to capture stereoscopic images, and a controller in operable communication with the endoscope. The controller is configured to execute instructions to cause the controller to analyze the stereoscopic images from the endoscope to identify a human-held tool in the stereoscopic images and to estimate a type and/or pose of the human-held tool, infer a position of a person holding the human-held tool based on the type and/or pose of the human-held tool, determine a spatial relationship between the person and the robotic linkage based on the inferred position of the person, and generate a warning of a potential collision between the person and the robotic linkage based on the determined spatial relationship.

In various embodiments of the system, the robotic linkage includes sensors configured to provide measurements of an angle and a velocity of each joint of the plurality of joints.

In various embodiments of the system, the robotic surgical system includes a robotic tool coupled to a distal portion of the robotic linkage. The controller is configured to execute the instructions to cause the controller to analyze the stereoscopic images from the endoscope to identify the robotic tool in the stereoscopic images and to estimate a pose of the robotic tool, and determine a swept volume of the robotic linkage based on the estimated pose of the robotic tool and based on the angle and the velocity of each joint of the plurality of joints, where the swept volume is determined without using any real-time image of the robotic linkage.

In various embodiments of the system, in analyzing the stereoscopic images, the instructions implement an artificial-intelligence learning machine to determine the pose of the robotic tool.

In various embodiments of the system, the swept volume is a physical space that the robotic linkage could move through in a particular time period based on the velocity of each joint of the plurality of joints.

In various embodiments of the system, in generating the warning of the potential collision, the instructions when executed cause the controller to determine the potential collision based on an overlap between the inferred position of the person and the swept volume of the robotic linkage.

In various embodiments of the system, in analyzing the stereoscopic images, the instructions implement an artificial-intelligence learning machine configured to determine the type and/or pose of the human-held tool.

In various embodiments of the system, in inferring the position of the person holding the human-held tool, the controller executes the instructions to cause the controller to access information relating to how the human-held tool is typically held during a particular phase of a surgical procedure, and infer the position of the person holding the human-held tool based further on the information relating to how the human-held tool is typically held during the particular phase of the surgical procedure.

In various embodiments of the system, in inferring the position of the person holding the human-held tool, the controller executes the instructions to cause the controller to access physical attribute information for the person holding the human-held tool, and infer the position of the person holding the human-held tool based further on the physical attribute information for the person holding the human-held tool, where the position of the person holding the human-held tool is inferred without using any real-time image of the person holding the human-held tool.

In accordance with aspects of the disclosure, a method is disclosed for warning of a potential collision between a person holding a human-held tool and a robotic surgical system having a robotic linkage including a plurality of joints. The method includes accessing stereoscopic images obtained by an endoscope coupled to a distal portion of the robotic linkage, analyzing the stereoscopic images from the endoscope to identify the human-held tool in the stereoscopic images and to estimate a type and/or pose of the human-held tool, inferring a position of the person holding the human-held tool based on the type and/or pose of the human-held tool, determining a spatial relationship between the person and the robotic linkage based on the inferred position of the person, and generating a warning of a potential collision between the person and the robotic linkage based on the determined spatial relationship.

In various embodiments of the method, the robotic linkage includes sensors configured to provide measurements of an angle and a velocity of each joint of the plurality of joints.

In various embodiments of the method, the robotic surgical system includes a robotic tool coupled to a distal portion of the robotic linkage, and the method includes analyzing the stereoscopic images from the endoscope to identify the robotic tool in the stereoscopic images and to estimate a pose of the robotic tool, and determining a swept volume of the robotic linkage based on the estimated pose of the robotic tool and based on the angle and the velocity of each joint of the plurality of joints, where the swept volume is determined without using any real-time image of the robotic linkage.

In various embodiments of the method, analyzing the stereoscopic images includes using an artificial-intelligence learning machine to determine the pose of the robotic tool.

In various embodiments of the method, the swept volume is a physical space that the robotic linkage could move through in a particular time period based on the velocity of each joint of the plurality of joints.

In various embodiments of the method, generating the warning of the potential collision includes determining the potential collision based on an overlap between the inferred position of the person and the swept volume of the robotic linkage.

In various embodiments of the method, analyzing the stereoscopic images includes using an artificial-intelligence learning machine configured to determine the type and/or pose of the human-held tool.

In various embodiments of the method, inferring the position of the person holding the human-held tool includes accessing information relating to how the human-held tool is typically held during a particular phase of a surgical procedure, and inferring the position of the person holding the human-held tool based further on the information relating to how the human-held tool is typically held during the particular phase of the surgical procedure.

In various embodiments of the method, inferring the position of the person holding the human-held tool includes accessing physical attribute information for the person holding the human-held tool, and inferring the position of the person holding the human-held tool based further on the physical attribute information for the person holding the human-held tool, where the position of the person holding the human-held tool is inferred without using any real-time image of the person holding the human-held tool.

In various embodiments of the method, a non-transitory computer readable medium includes computer executable instructions which, when executed by a controller, cause the controller to perform a method for warning of a potential collision between a person holding a human-held tool and a robotic surgical system having a robotic linkage including a plurality of joints. The method includes accessing stereoscopic images obtained by an endoscope coupled to a distal portion of the robotic linkage, analyzing the stereoscopic images from the endoscope to identify the human-held tool in the stereoscopic images and to estimate a type and/or pose of the human-held tool, inferring a position of the person holding the human-held tool based on the type and/or pose of the human-held tool, determining a spatial relationship between the person and the robotic linkage based on the inferred position of the person, and generating a warning of a potential collision between the person and the robotic linkage based on the determined spatial relationship.

In various embodiments of the non-transitory computer readable medium, the computer executable instructions, when executed by the controller, cause the controller to further perform the method for warning of a potential collision, including analyzing the stereoscopic images from the endoscope to identify a robotic tool in the stereoscopic images and to estimate a pose of the robotic tool, where the robotic tool is coupled to a distal portion of the robotic linkage, and determining a swept volume of the robotic linkage based on the estimated pose of the robotic tool and based on an angle and a velocity of each joint of the plurality of joints, where generating the warning of the potential collision includes determining the potential collision based on an overlap between the inferred position of the person and the swept volume of the robotic linkage.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Surgeries with a robotic surgical system use a non-robotic/human-held tool under certain situations, giving rise to potential collisions between the robotic surgical system and a person holding the non-robotic tool. In accordance with aspects of the present disclosure, such potential collisions can be mitigated by determining a spatial relationship between the person and the robotic surgical system. The person's position may be inferred based on stereoscopic images from an endoscope, and a swept volume for the robotic surgical system may be determined based on joint angles and velocities of the robotic surgical system. Based on an overlap between the position of a person and the swept volume, potential collisions can be determined. Appropriate controls may be performed to reduce the potential collisions. As described in more detail below, the type of the human-held tool and/or the pose/orientation of the human-held tool is the starting point for determining the position of the person holding the human-held tool. Thus, the techniques disclosed herein for determining the position of a person holding a non-robotic tool is not based on an image of the person.

Figure 1A:
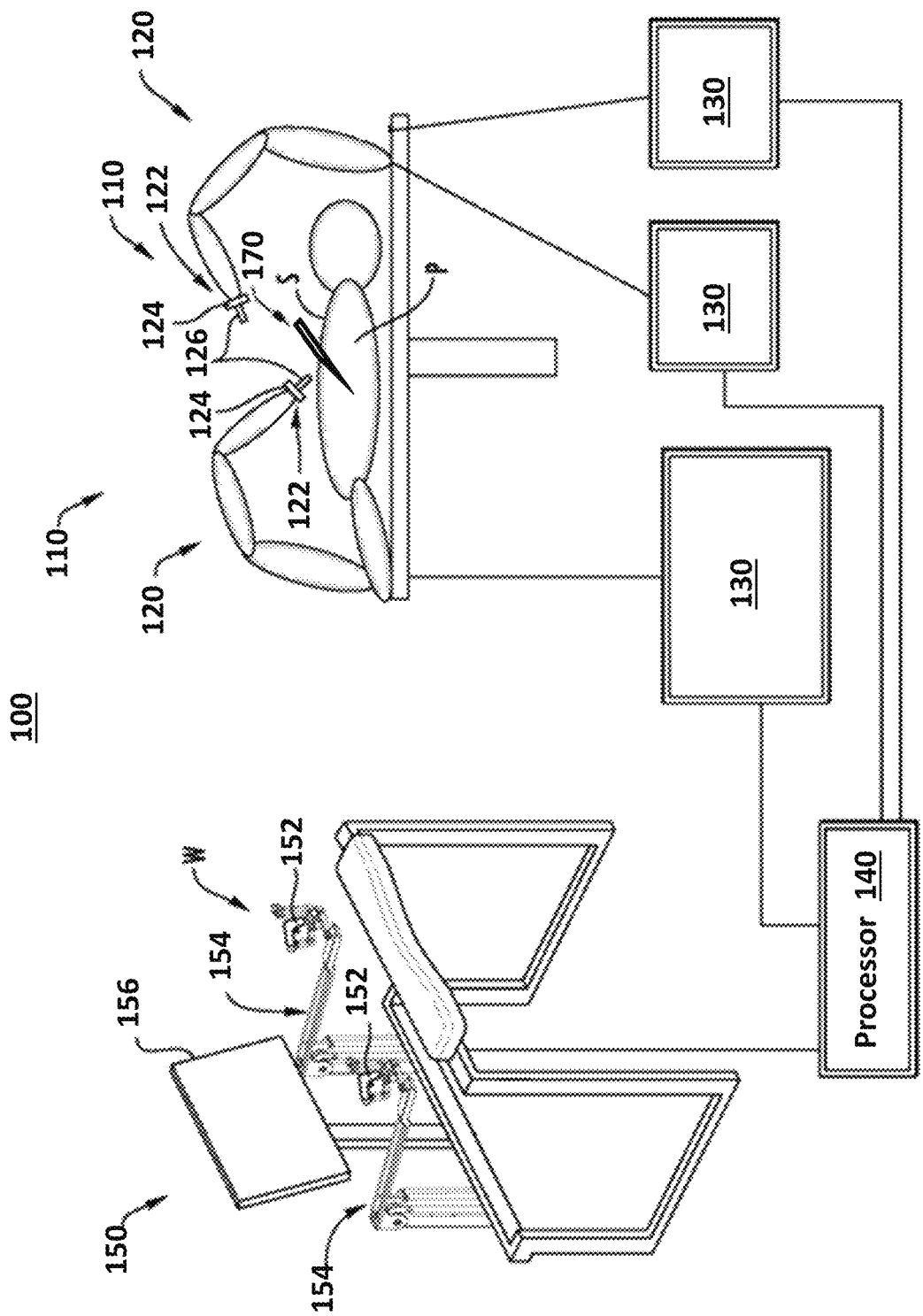
FIG. 1A is a diagram of an exemplary robotic surgical system, in accordance with embodiments of the disclosure.
Figure 1B:
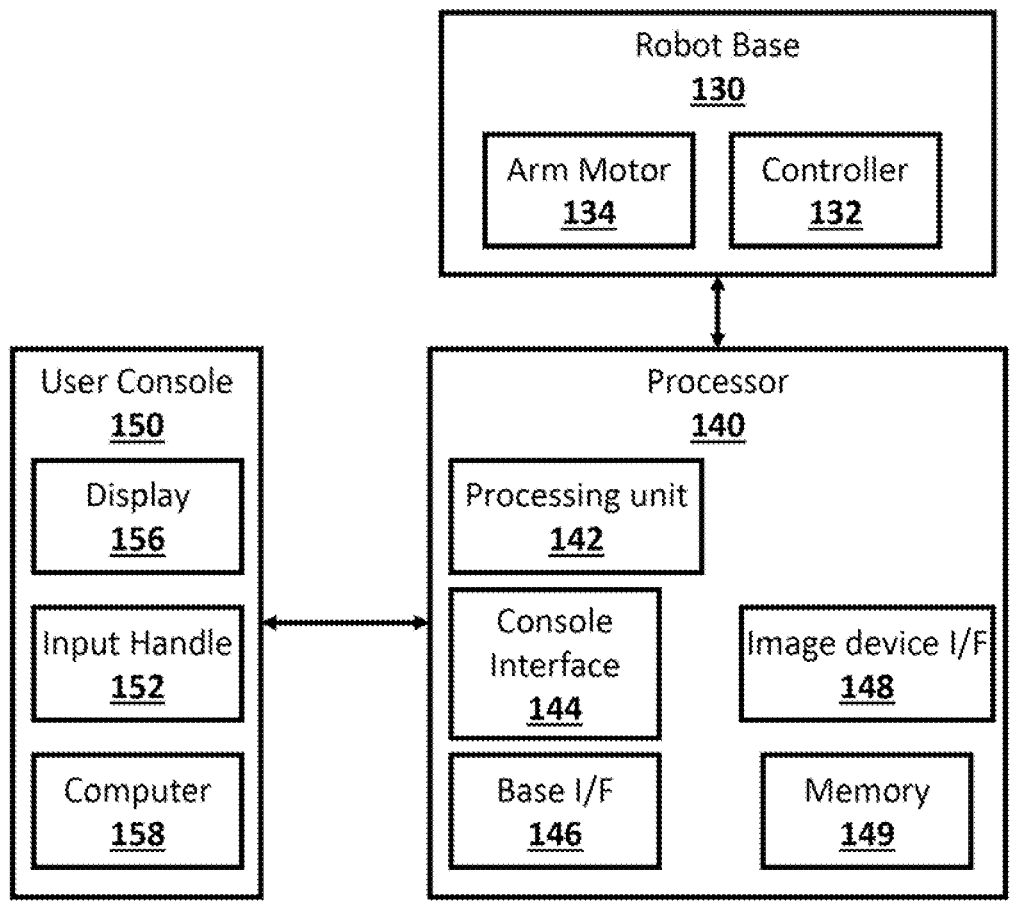
FIG. 1B is a block diagram of the robotic surgical system of FIG. 1A, in accordance with embodiments of the disclosure.

Referring to FIGS. 1A and 1B, there is shown a diagram of an exemplary robotic surgical system 100 used in conjunction with a non-robotic/human-held tool 170. The robotic surgical system includes a surgical robot 110, a processor 140, and a user console 150. The robotic surgical system 100 may not be able to completely perform a surgery by itself and may be supplemented by use of non-robotic/human-held tools 170. The surgical robot 110 generally includes one or more robotic linkages or arms 120 and robot bases 130 which support the corresponding robotic linkages 120. Each robotic linkage 120 is moveable at or around joints. For example, a distal robotic linkage 120 has an end 122 that supports the end effector or tool 126, which is configured to act on a target of interest. In addition, an imaging device 124 for imaging a surgical site "S" may be installed at the end 122 of the distal robotic linkage 120.

The user console 150 is in communication with the robot bases 130 through the processor 140. In addition, each robot base 130 may include a controller 132, which is in communication with the processor 140, and an arm motor 134, as shown in FIG. 1B. The robotic linkage 120 may include one or more arms, and joints between two adjoining arms. The arm motor 134 may be configured to actuate each joint of the robotic linkage 120 to move the end effector 126 to intended positions according to the clinician's controls.

In accordance with aspects of the present disclosure, each joint of the robotic linkages 120 may have one or more sensors configured to sense an angle between two adjoining arms and to sense a velocity of each arm or angular velocity of each joint. Such sensed information may be transmitted to the processor 140, which then performs calculations to identify a swept volume of each of the robotic linkages 120. The swept volume may indicate a volume of space that each of the robotic linkages 120 may occupy within a period of time.

The non-robotic/human-held tool 170 may be held by a person who occupies a space in the surgery room next to the robotic surgical system 100. Thus, there is a possibility that the person and the robotic surgical system 100 might collide or interfere with each other. Such collisions may lead to unexpected movements of the robotic and non-robotic tools, resulting in potential injury to the patient or the person holding the non-robotic tool. As described later herein, the processor 140 may determine a possibility of potential collision between the person and the robotic linkages 120. The processor 140 may further display a popup window on a display device 156 of the user console 150 to provide a warning of the potential collision. The warning may include an audible sound or haptic vibrations to an input handle 152.

Figure 2:
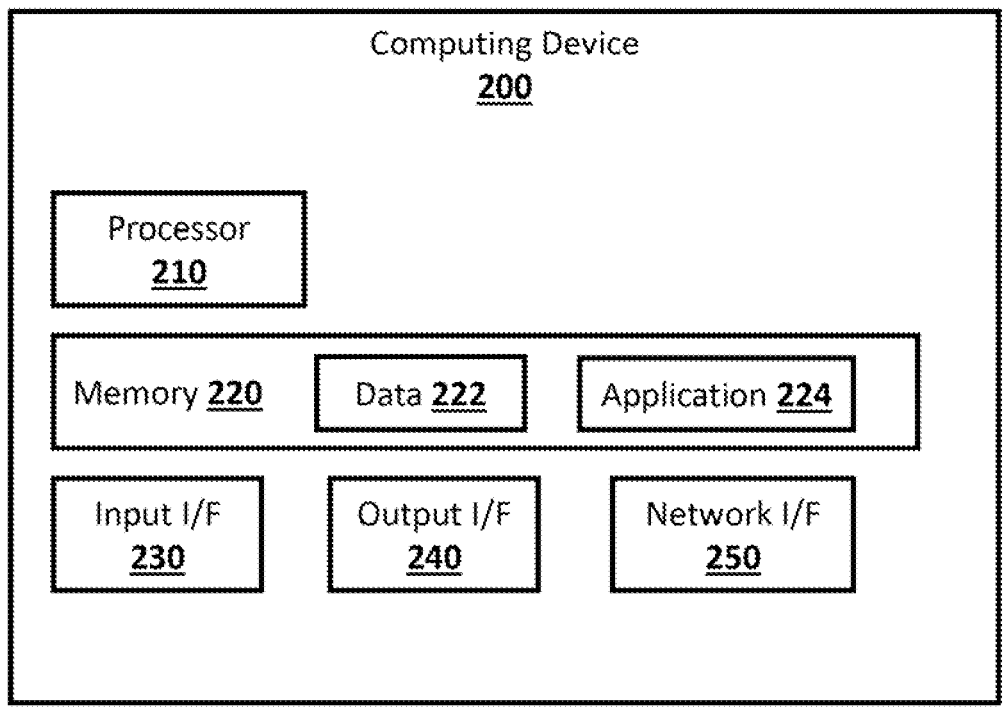
FIG. 2 is a block diagram of an exemplary computing device, in accordance with embodiments of the disclosure.

Now referring to FIG. 1B, the processor 140 may be a stand-alone computing device similar to the computing device 200 of FIG. 2, or integrated into one or more of the various components of the robotic surgical system 100 (e.g., in the robot bases 130 or the user console 150). The processor 140 may also be distributed to multiple components of the robotic surgical system 100 (e.g., in multiple robot bases 130). The processor 140 of the robotic surgical system 100 generally includes a processing unit 142, a memory 149, the robot base interface 146, a console interface 144, and an image device interface 148. The robot base interface 146, the console interface 144, and the image device interface 148 communicate with the robot bases 130, the user console 150, the imaging devices 124 via either wireless configurations, e.g., Wi-Fi, Bluetooth, LTE, and/or wired configurations. Although depicted as a separate module, the console interface 144, the robot base interface 146, and the image device interface 148 may be a single component in other embodiments.

The user console 150 also includes input handles 152 which are supported on control arms 154 which allow a clinician to manipulate the surgical robot 110 (e.g., move the robotic linkages 120, the ends 122 of the robotic linkages 120, and/or the tools 126). Each of the input handles 152 is in communication with the processor 140 to transmit control signals thereto and to receive feedback signals therefrom. Additionally or alternatively, each of the input handles 152 may include input devices (not explicitly shown) which allow the surgeon to manipulate (e.g., clamp, grasp, fire, open, close, rotate, thrust, slice, etc.) the tools 126 supported at the ends 122 of the robotic linkages 120.

Each of the input handles 152 is moveable through a predefined workspace to move the ends 122 of the robotic linkages 120, e.g., tools 126, within the surgical site "S". The three-dimensional images on the display device 156 are orientated such that the movement of the input handles 152 moves the ends 122 of the robotic linkages 120 as viewed on the display device 156. The three-dimensional images remain stationary while movement of the input handles 152 is scaled to movement of the ends 122 of the robotic linkages 120 within the three-dimensional images. To maintain an orientation of the three-dimensional images, kinematic mapping of the input handles 152 is based on a camera orientation relative to an orientation of the ends 122 of the robotic linkages 120. The orientation of the three-dimensional images on the display device 156 may be mirrored or rotated relative to the view captured by the imaging devices 124. In addition, the size of the three-dimensional images on the display device 156 may be scaled to be larger or smaller than the actual structures of the surgical site "S" permitting the clinician to have a better view of internal structures within the surgical site "S". As the input handles 152 are moved, the tools 126 are moved within the surgical site "S" as detailed below. Movement of the tools 126 may also include movement of the ends 122 of the robotic linkages 120 which support the tools 126.

The user console 150 further includes a computer 158, which includes a processing unit or processor and memory, which includes data, instructions and/or information related to the various components, algorithms, and/or operations of the robot bases 130, similar in many respects to the computing device 200 of FIG. 2. The user console 150 may operate using any suitable electronic service, database, platform, cloud, or the like. The user console 150 is in communication with the input handles 152 and a display device 156. Each input handle 152 may, upon engagement by the clinician, provides input signals to the computer 158 corresponding to the movement of the input handles 152. Based on the received input signals, the computer 158 may process and transmit the signals to the processor 140, which in turn transmits control signals to the robot bases 130, and the devices of the robot bases 130, to effect motion based at least in part on the signals transmitted from the computer 158. The input handles 152 may be handles, pedals, or computer accessories (e.g., a keyboard, joystick, mouse, button, touch screen, switch, trackball, and the like).

The user console 150 includes the display device 156 configured to display two-dimensional and/or three-dimensional images of the surgical site "S", which may include data captured by the imaging devices 124 positioned on the ends 122 of the robotic linkages 120. The imaging devices 124 may capture visual images, infra-red images, ultrasound images, X-ray images, thermal images, and/or any other known real-time images of the surgical site "S". The imaging devices 124 transmit captured imaging data to the processor 140 which creates three-dimensional images of the surgical site "S" in real-time from the imaging data and transmits the three-dimensional images to the display device 156 for displaying such.

The display device 156 may be connected to an endoscope installed on the end 122 of the robotic linkages 120 so that live view images from the endoscope may be displayed on the display device 156. Further, as described above, a potential warning may be displayed in an overlapping manner over the live view images. The endoscope may capture images of the non-robotic/human-held tool 170. Such captured images of the non-robotic/human-held tool 170 are transmitted to and processed by the processor 140 so that a pose and/or a type of the non-robotic/human-held tool 170 may be determined. Such information may be used to determine a volume occupied by the person or a position of the person who holds the non-robotic/human-held tool 170. The person's volume/position and the swept volume may be compared to determine a potential collision between the robotic surgical system 100 and the person.

Referring now to FIG. 2, a block diagram of an exemplary computing device is shown and is designated generally as a computing device 200. Though not explicitly shown in the corresponding figures of the present disclosure, the computing device 200, or one or more components thereof, may represent one or more components (e.g., the processor 140 or the computer 158) of the robotic surgical system 100. The computing device 200 may include one or more processors 210, one or more memories 220, input interface 230, output interface 240, network interface 250, or any desired subset of components thereof.

The memory 220 includes non-transitory computer-readable storage media for storing data and/or software which include instructions that may be executed by the one or more processors 210. When executed, the instructions may cause the processor 210 to control operation of the computing device 200 such as, without limitation, reception, analysis, and transmission of sensor signals received in response to movement and/or actuation of the one or more input handles 152. The memory 220 may include one or more solid-state storage devices such as flash memory chips. Additionally, or alternatively, the memory 220 may include one or more mass storage devices in communication with the processor 210 through a mass storage controller and a communications bus (not shown). Although the description of computer readable media described in this disclosure refers to a solid-state storage device, it will be appreciated by one of ordinary skill that computer-readable media may include any available media that can be accessed by the processor 210. More particularly, the computer readable storage media may include, without limitation, non-transitory, volatile, non-volatile, removable, non-removable media, and the like, implemented in any method of technology for storage of information such as computer readable instructions, data structures, program modules, or other suitable data access and management systems. Examples of computer-readable storage media include RAM, ROM, EPROM, EEPROM, flash memory, or other known solid state memory technology, CD-ROM, DVD, Blu-Ray, or other such optical storage, magnetic cassettes, magnetic tape, magnetic disk storage or other magnetic storage devices, or any other medium which may be used to store information and which can be accessed by the computing device 200.

In embodiments, the memory 220 stores data 222 and/or one or more applications 224. The data 222 can include information about various robotic tools and various human-held tools, such as dimensions of such tools. Use of such data 222 will be described in more detail in connection with FIG. 3. The applications 224 may include instructions which are executed on the one or more processors 210 of the computing device 200. The applications 224 may include instructions which cause an input interface 230 and/or an output interface 240 to receive and transmit sensor signals, respectively, to and from the various components of the robotic surgical system 100. Additionally or alternatively, the computing device 200 may transmit the signals for analysis and/or display via the output interface 240. For example, the memory 220 may include instructions which, when executed, generate a depth map or point cloud of the objects within the surgical environment based on the real-time image data received from the image devices of the robotic surgical system 100. The depth map or point cloud may be stored in the memory 220 across multiple iterations for a later cumulative analysis of the depth maps or point clouds. In various embodiments, the computing device 200 can include data 222 and applications 224 which implement a trained learning machine, such as a convolutional neural network. In various embodiments, the trained learning machine can process images of a surgical site to identify surgical tools and determine the pose/orientation of the tools, as discussed in more detail in connection with FIG. 3.

Additionally, in accordance with aspects of the present disclosure, the memory 220 may include instructions that, when executed by the processor 210, identify potential collisions between a person and the robotic surgical system 100. Techniques for identifying a potential collision will be described later herein. The output interface 240 may transmit the sensor signals to a display device such as the display device 156 of the user console 150, or a remote display located in the surgical environment and in communication with the computing device 200, to display an indication that a collision may occur.

The output interface 240 may further transmit and/or receive data via a network interface 250 via one or more wireless configurations, e.g., radio frequency, optical, Wi-Fi®, Bluetooth® (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE® 802.15.4-2003 standard for wireless personal area networks (WPANs)). Although depicted as a separate component, the network interface 250 may be integrated into the input interface 230 and/or the output interface 240.

Figure 3:
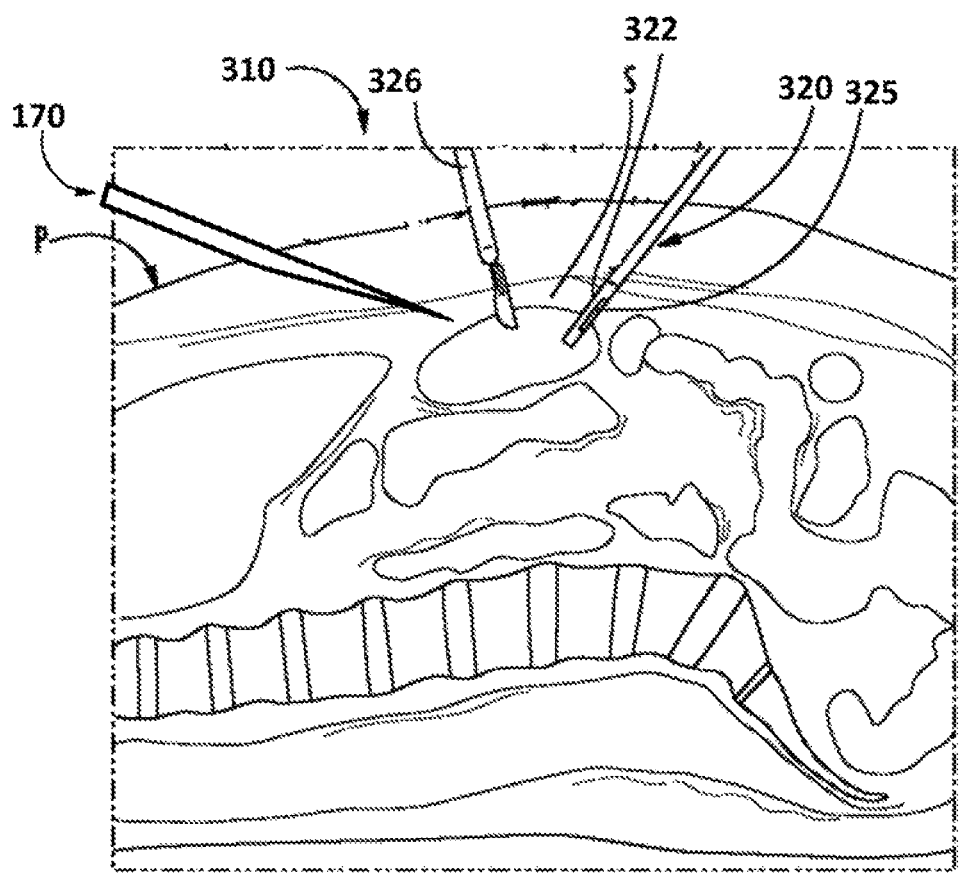
FIG. 3 is a diagram of an exemplary surgical area illustrating an endoscope within a body cavity of a patient, in accordance with embodiments of the disclosure.

With additional reference to FIG. 3, there is shown a diagram of an exemplary surgical procedure 310 using the robotic surgical system 100 of FIG. 1A, including an endoscope 320 which is inserted through a body cavity of the patient "P" and is configured to provide optical views or images of the surgical site "S" and to transmit the optical images to the display device 156. The endoscope 320 includes a camera 322 to capture images of the surgical site "S" during a procedure as detailed below. The surgical procedure 310 also includes a robotic tool 326 of the robotic surgical system and a human-held non-robotic/human-held tool 170.

In an aspect, the camera 322 may be a stereoscopic camera such that the captured images provide depth information that can be used to determine positions/orientations of organs, the robotic tool 326, and/or the non-robotic/human-held tool 170. Further, the stereoscopic images having depth information may be used to identify a pose and/or a type of the non-robotic/human-held tool 170 captured therein.

The endoscope 320 is inserted through an opening, either a natural opening or an incision, to position the camera 322 within the body cavity adjacent the surgical site "S" to allow the camera 322 to capture images of the surgical site "S". The camera 322 transmits the captured images to the processor 140. The processor 140 receives the images or data of the surgical site "S" from the camera 322 and displays the received images on the display device 156 such that a clinician can visualize the surgical site "S". In various embodiments, the endoscope 320 and/or camera 322 includes a sensor 325 that indicates the pose of the camera 322 as the images of the surgical site "S" are captured. The sensor 325 is in communication with the processor 140 such that the processor 140 receives the pose of the camera 322 from the sensor 325 and associates the pose of the camera 322 with the images captured by the camera 322. In various embodiments, the sensor 325 may sense six degrees of freedom, including X, Y, and Z axes, as well as pitch, roll, and yaw.

The surgical diagram of FIG. 3 is exemplary, and in various embodiments, more than one endoscope 320 or more than one camera 322 can be used. For convenience, a procedure using a single endoscope and a single camera 322 will be described below. However, it will be understood that the aspects and embodiments described herein apply to procedures involving multiple endoscopes or cameras, as well.

In accordance with aspects of the present disclosure, the camera 322 may capture images of the surgical site "S" and can capture images of the non-robotic/human-held tool 170 and the robotic tool 326. The images from the camera 322 may be used to identify a position, a pose, and/or a type of the non-robotic/human-held tool 170. As mentioned above, the camera 322 can be a stereoscopic camera that provides depth information, which can be used to determine the pose/orientation of the non-robotic/human-held tool 170 in the surgical site S. In various embodiments, and as mentioned above, a computing device (e.g., 200, FIG. 2) can implement a trained learning machine that can process the images from the camera 322 to determine the pose and/or the type of the non-robotic/human-held tool 170. In various embodiments, learning machines such as convolutional neural networks can be trained to recognize and identify objects, and such neural networks can be applied to identify the non-robotic/human-held tool 170. Additionally, learning machines can also be trained to identify other aspects of the tool, such as pose/orientation. In various embodiments, depth information in the stereoscopic images captured by the camera 322 can be processed by a trained learning machine to identify a pose or orientation of the non-robotic/human-held tool 170. In various embodiments, pose information from the sensor 325 of the endoscope 320 can also be input to and processed by the trained learning machine to determine the pose/orientation of the non-robotic/human-held tool 170. The learning machine described above is exemplary, and other types or implementations of machine learning are contemplated to be within the scope of the present disclosure.

In accordance with aspects of the present disclosure, the position of the person holding the non-robotic/human-held tool 170 can be inferred based on the type and/or the pose of the non-robotic/human-held tool 170. Thus, the type of the non-robotic/human-held tool 170 and/or the pose/orientation of the non-robotic/human-held tool 170 are the starting point for inferring the position of the person holding the non-robotic/human-held tool 170. Accordingly, the disclosed techniques for determining the position of the person holding the non-robotic/human-held tool 170 are not based on an image of the person.

In various embodiments, identifying the type of the non-robotic/human-held tool 170 may be sufficient to infer the position of the person holding the tool. For example, if there is one particular way to orient and hold the identified non-robotic/human-held tool 170, then identifying the particular non-robotic/human-held tool 170 would provide an inference with regard to the position of the person holding the non-robotic/human-held tool 170.

In various embodiments, when the non-robotic/human-held tool 170 can have various orientations, the orientation of the non-robotic/human-held tool 170 can be determined from the stereoscopic images of the camera 322 using a trained learning machine, as described above. Different orientations of the non-robotic/human-held tool 170 can correspond to different ways of holding the non-robotic/human-held tool 170 and correspond to different positions of the person holding the non-robotic/human-held tool 170. In various embodiments, such correspondence can be stored in a database (e.g., 222, FIG. 2), for each of the possible orientations of the non-robotic/human-held tool 170. In various embodiments, a trained learning machine can predict a position of the person holding the non-robotic/human-held tool 170 based on the pose/orientation of the non-robotic/human-held tool 170. Such a learning machine can be trained using training data relating to the pose/orientation of human-held tools and which are tagged with information relating to the position of the person holding such tools.

In an aspect, the position of the person holding the hand-held tool can be inferred based on personal dimensions of the person holding the tool, such as height dimensions and/or arm dimensions, among other dimensions. Such personal dimension information can be stored in a database of such information (e.g., 222, FIG. 2). The database can include such dimensional information for each person who is assigned to the surgical procedure and who could be tasked with holding the non-robotic/human-held tool 170. The processor 140 may access the database and infer the position of the person holding the non-robotic/human-held tool 170 based on the personal information.

The position of a person holding a non-robotic tool can be represented in various ways. In various embodiments, the position can be represented as a cylindrical volume or as another three-dimensional volume. In various embodiments, the position can be represented by a more detailed model, such as a volume including protrusions corresponding to appendages or other body positions. Such possible ways of representing a person's position are exemplary, and other variations are contemplated to be within the scope of the disclosure.

In accordance with aspects of the disclosure, and with continuing reference to FIG. 3, the techniques described above for identifying a type and/or pose of a human-held tool is also applied to identifying a type and/or pose of a robotic tool 326. The physical position of the robotic linkage coupled to the robotic tool 326 (e.g., 120, FIG. 1) can be determined based on the type and/or the pose of the robotic tool 326. Thus, the type of the robotic tool 326 and/or the pose/orientation of the robotic tool 326 are the starting point for determining the position of the robotic linkage coupled to the robotic tool 326. Accordingly, the disclosed techniques for determining the position of the robotic linkage coupled to the robotic tool 326 are not based on an image of the robotic system (100, FIG. 1) nor based on any information about the position of the robotic system in physical space. Rather, as explained below, the disclosed techniques are based on an image of the robotic tool 326 at the surgical site and are based on information of the robotic system 100 on the angle and velocity of each joint of the robotic linkages.

The images from the camera 322 can capture images of the robotic tool 326 at the surgical site. In various embodiments, a computing device (e.g., 200, FIG. 2) can implement a trained learning machine that can process the images from the camera 322 to determine the pose and/or the type of the robotic tool 326. In various embodiments, learning machines such as convolutional neural networks can be trained to recognize and identify objects, and such neural networks can be applied to identify the robotic tool 326. Additionally, learning machines can also be trained to identify other aspects of the tool, such as pose/orientation. In various embodiments, depth information in the stereoscopic images captured by the camera 322 can be processed by a trained learning machine to identify a pose or orientation of the robotic tool 326. In various embodiments, pose information from the sensor 325 of the endoscope 320 can also be input to and processed by the trained learning machine to determine the pose/orientation of the robotic tool 326. The learning machine described above is exemplary, and other types or implementations of machine learning are contemplated to be within the scope of the present disclosure.

With reference also to FIG. 1A, the processor 140 accesses information on angles between each joint of the linkages or robotic arms 120 and angular velocities of each joint. Based on the received information from the robotic linkages 120, the processor 140 is to able apply such information to the type and/or pose of the robotic tool 326 to determine the position of each portion of the robotic linkages 120 and to determine a swept volume of the robotic surgical system 100, which is a volume of space that the robotic surgical system 100 can occupy during a time period. In various embodiments, dimensions of the robotic tool 326 can be stored in a database (e.g., 222, FIG. 2), and dimension of the robotic linkages 120 can also be stored in the database. After identifying the type and/or pose of the robotic tool 326, the dimensions of the robotic tool 326 can be retrieved from the database and the entire position of the robotic tool 326 can be determined. Using the joint angles and arm dimensions, the position of each linkage of the robotic arm coupled to the robotic tool 326 can be determined. Then, the velocity of each joint can be used to project the motion of the robotic linkages 120 forward in time, to determine the swept volume of the robotic linkages 120 and the robotic system 100.

In various embodiments, when the distance between the swept volume of the robotic surgical system 100/robotic linkage 120 and the inferred position of the person is less than or equal to a threshold distance, the processor 140 determines that a potential collision can occur. The threshold distance can be, for example, 3 inches or 6 inches, or another distance. The distance can be computed using, for example, the closest portions of the swept volume and the inferred position of the person. In various embodiments, when the swept volume of the robotic surgical system 100/robotic linkage 120 overlaps with the inferred position of the person holding the non-robotic/human-held tool 170, the processor 140 determines that a potential collision can occur. In case of a potential collision, the processor 140 may overlay a warning window over the display device 156. In an aspect, the warning may be a haptic vibration feedback on the input handle 152, an audio warning, red-flashes on the display device 156, or any combination thereof.

When potential collisions are to be differentiated from an imminent collision, there are two thresholds—one for potential collisions and the other one for the imminent collision. For example, an imminent collision can be based on the swept volume and the inferred position of the person overlapping with each other, whereas a potential collision can be based on the swept volume and the inferred position of the person not overlapping but being within a threshold distance of each other. In this case of an imminent collision, the processor 140 may immediately stop movement of the robotic surgical system 100 to reduce the chance of such an imminent collision. In various embodiments, the processor 140 may decrease a maximum torque of the motor 134 as the robotic arm 120 is close to the imminent collision, or decrease speed limits, acceleration limits, or maximum external torques that can be produced, where the external torque is equal to subtract an actuator torque and a gravitational torque from a dynamic torque of the robotic arm 120.

In an aspect, the processor 140 may change a damping gain in controlling the position or the angular velocity of the robotic arm 120 such that the controller 132 becomes smoother in the direction that the imminent/potential collision may occur. Also, the processor 140 may increase a scaling factor so as to decrease the angular velocity and to provide more reaction time as the haptic/visual/audio feedback is provided.

Figure 4:
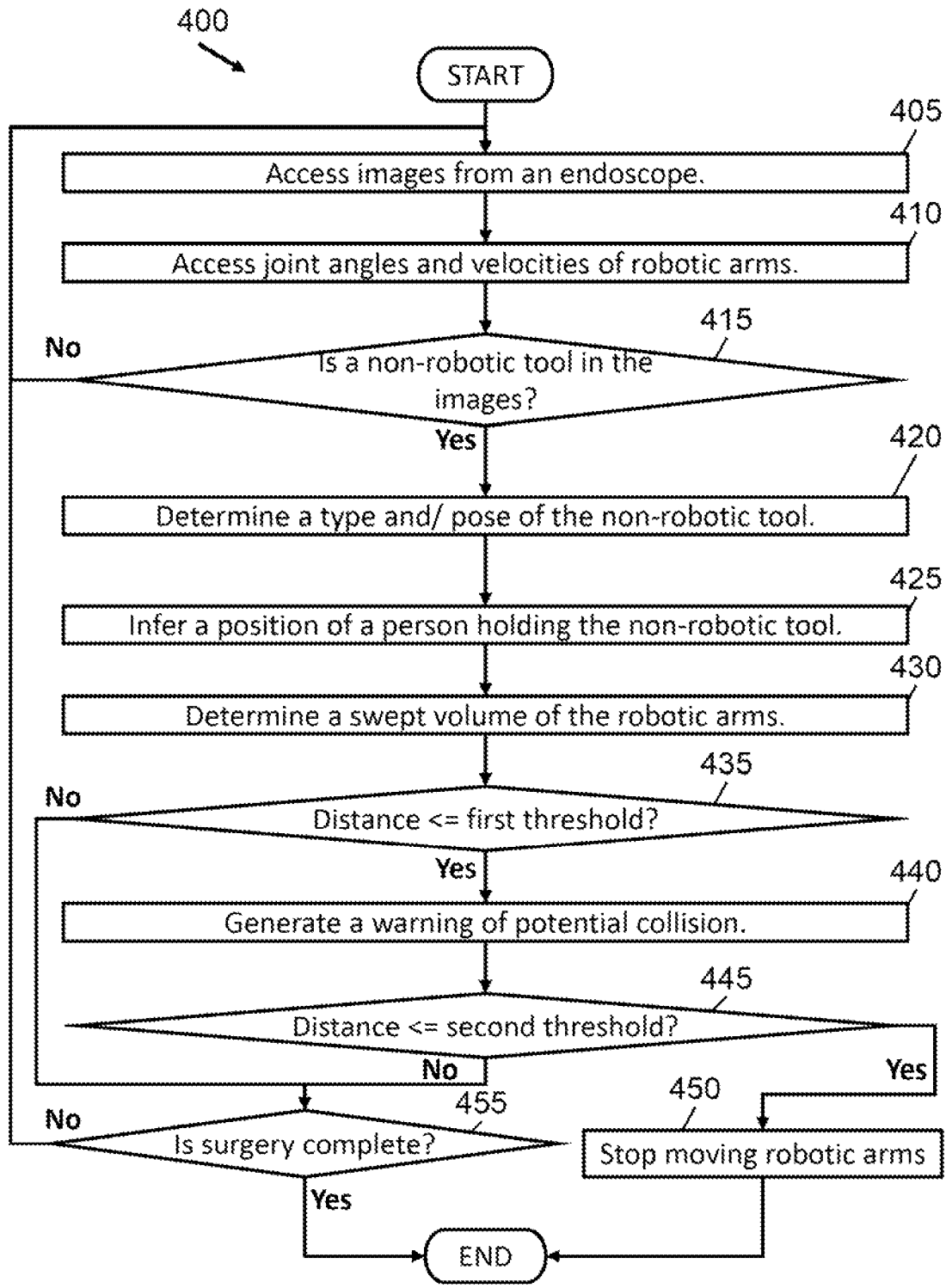
FIG. 4 is a flowchart of an exemplary operation for controlling a robotic surgical system, in accordance with embodiments of the disclosure.

FIG. 4 is a flowchart illustrating a method 400 for mitigating a potential collision during a robotic surgery in accordance with embodiments of the disclosure. When an end portion of a robotic linkage is inserted through an incision or orifice of a patient, an endoscope disposed at the end portion of the robotic linkage may capture images of a surgical site. The method 400 starts by accessing images from the endoscope within the surgical site in step 405. The endoscope may include a stereoscopic imaging device, which captures stereoscopic images.

The robotic linkage includes a plurality of arms, between which a joint connects. The link may include one or more sensors, which sense an angle between the connected arms and a velocity thereof. In step 410, joint angles and velocities of a robotic arm are received. Such information may include an angle between two connected arms of a joint of the robotic linkage and a velocity of each joint. In an aspect, the velocity may be an angular velocity of each joint.

In step 415, it is determined whether or not a non-robotic tool 170 is captured in the images. When it is determined that the non-robotic tool 170 is not captured in the images, the method 400 goes back to step 405.

When it is determined that the non-robotic tool 170 is captured in the images in step 415, a type and/or pose of the non-robotic tool 170 may be determined in step 420. The stereoscopic images include depth information, which may be processed to identify the pose of the non-robotic tool 170 positioned within the surgical site. Based on the type and/or pose of the non-robotic tool 170, a position of a person holding the non-robotic tool 170 may be inferred in step 425. In a case when the position of the person cannot be determine based on the stereoscopic images, a predetermined or default position of the person holding the non-robotic tool 170 can be used as the inferred position of the person. This may occur, for example, when the type or pose of the non-robotic tool 170 is not identifiable in the stereoscopic images.

In step 430, the swept volume of the robotic linkage 120 may be determined. The type and/or pose of a robotic tool 326 at the surgical site can be determined based on an image of the robotic tool 326 at the surgical site. The angle of each joint and dimension of each arm segment (or robotic linkage 120) can be used to determine the positions of the robotic linkage 120 by starting the determination from the type and/or pose of the robotic tool 326. The velocity of each joint can be used to determine the swept volume of the robotic linkage 120. The swept volume is a volume of space that can be occupied by the robotic linkage 120 during a time frame. The time frame can vary and can be, for example, 1 second or 3 seconds or another time period. The angular velocity of each joint includes a direction and an angular speed. Thus, the angular travel distance of each joint and each arm or linkage can be calculated in the direction and the corresponding swept volume can be then calculated. Based on the configuration (e.g., connection structure of each joint) of the robotic linkage 326, the swept volume of the robotic linkage 326 may be determined by combining the swept volume of each joint. Thus, the swept volume of the robotic linkage 326 is determined from calculating the swept volume of each arm or linkage.

The distance or overlap between the swept volume and the inferred position of the person may be the shortest distance between the position of the person and the swept volume. At step 435, the distance between the volume of the person and the swept volume is compared with the first threshold. When it is determined that the distance is less than or equal to the first threshold, a warning of potential collision is generated in step 440. The warning may be haptic vibrations on an input handle of the robotic linkage, a visual warning overlaid on a display of the robotic surgical system, or an audible warning. The listing of warnings is not meant to be limiting but may include any other suitable means as readily appreciated by a person having ordinary skill in the art.

At step 445, it is further determined whether or not the distance is less than or equal to a second threshold. In a case when the distance is determined to be less than or equal to the second threshold, the movement of the robotic linkage 326 is stopped in step 450. The second threshold is a value indicating an imminent collision, meaning that the robotic linkage is about to collide with the person or another robotic linkage 326. Thus, in this situation, the robotic linkage 326 stops movement to reduce the chance of the imminent collision, in step 450. The method 400 then ends. In an aspect, after stopping movements of the robotic linkage 326, the clinician may adjust the settings of the robotic linkage 326 or position of the person and re-initiate the method 400 again.

When it is determined that the distance is greater than the second threshold in step 445, it is further determined whether or not the surgery is complete in step 455. When the surgery is not completed, steps 405-455 are repeated until the surgery is completed.

When it is determined that the surgery is completed in step 455, the method 400 ends. In this way, the surgery with the robotic surgical system and the non-robotic tool 170 can be performed while mitigating potential collisions between the robotic system 100 and a person holding a non-robotic tool 170.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A robotic surgical system comprising:
    a robotic linkage including a plurality of joints;
    an endoscope coupled to a distal portion of the robotic linkage and configured to capture stereoscopic images; and
    a controller in operable communication with the endoscope, the controller configured to execute instructions to cause the controller to:
        analyze the stereoscopic images from the endoscope to identify a human-held tool in the stereoscopic images and to estimate at least one of a type or pose of the human-held tool,
        infer a position of a person holding the human-held tool based on the at least one of the type or pose of the human-held tool,
        determine a spatial relationship between the person and the robotic linkage based on the inferred position of the person, and
        generate a warning of a potential collision between the person and the robotic linkage based on the determined spatial relationship.

2. The robotic surgical system according to claim 1, wherein the robotic linkage further includes sensors configured to provide measurements of an angle and a velocity of each joint of the plurality of joints.

3. The robotic surgical system according to claim 2, further comprising a robotic tool coupled to a distal portion of the robotic linkage,
    wherein the controller is configured to execute the instructions to further cause the controller to:
        analyze the stereoscopic images from the endoscope to identify the robotic tool in the stereoscopic images and to estimate a pose of the robotic tool, and
        determine a swept volume of the robotic linkage based on the estimated pose of the robotic tool and based on the angle and the velocity of each joint of the plurality of joints,
    wherein the swept volume is determined without using any real-time image of the robotic linkage.

4. The robotic surgical system according to claim 3, wherein in analyzing the stereoscopic images, the instructions implement an artificial-intelligence learning machine to determine the pose of the robotic tool.

5. The robotic surgical system according to claim 3, wherein the swept volume is a physical space that the robotic linkage could move through in a particular time period based on the velocity of each joint of the plurality of joints.

6. The robotic surgical system according to claim 3, wherein in generating the warning of the potential collision, the instructions when executed cause the controller to determine the potential collision based on an overlap between the inferred position of the person and the swept volume of the robotic linkage.

7. The robotic surgical system according to claim 1, wherein in analyzing the stereoscopic images, the instructions implement an artificial-intelligence learning machine configured to determine the at least one of the type or pose of the human-held tool.

8. The robotic surgical system according to claim 1, wherein in inferring the position of the person holding the human-held tool, the controller executes the instructions to cause the controller to:
   access information relating to how the human-held tool is typically held during a particular phase of a surgical procedure; and
   infer the position of the person holding the human-held tool based further on the information relating to how the human-held tool is typically held during the particular phase of the surgical procedure.

9. The robotic surgical system according to claim 8, wherein in inferring the position of the person holding the human-held tool, the controller executes the instructions to cause the controller to:
   access physical attribute information for the person holding the human-held tool; and
   infer the position of the person holding the human-held tool based further on the physical attribute information for the person holding the human-held tool,
   wherein the position of the person holding the human-held tool is inferred without using any real-time image of the person holding the human-held tool.

10. A method for warning of a potential collision between a person holding a human-held tool and a robotic surgical system having a robotic linkage including a plurality of joints, the method comprising:
    accessing stereoscopic images obtained by an endoscope coupled to a distal portion of the robotic linkage;
    analyzing the stereoscopic images from the endoscope to identify the human-held tool in the stereoscopic images and to estimate at least one of a type or pose of the human-held tool;
    inferring a position of the person holding the human-held tool based on the at least one of the type or pose of the human-held tool;
    determining a spatial relationship between the person and the robotic linkage based on the inferred position of the person; and
    generating a warning of a potential collision between the person and the robotic linkage based on the determined spatial relationship.

11. The method according to claim 10, wherein the robotic linkage further includes sensors configured to provide measurements of an angle and a velocity of each joint of the plurality of joints.

12. The method according to claim 10, wherein the robotic surgical system further includes a robotic tool coupled to a distal portion of the robotic linkage, the method further comprising:
    analyzing the stereoscopic images from the endoscope to identify the robotic tool in the stereoscopic images and to estimate a pose of the robotic tool; and
    determining a swept volume of the robotic linkage based on the estimated pose of the robotic tool and based on the angle and the velocity of each joint of the plurality of joints,
    wherein the swept volume is determined without using any real-time image of the robotic linkage.

13. The method according to claim 12, wherein analyzing the stereoscopic images includes using an artificial-intelligence learning machine to determine the pose of the robotic tool.

14. The method according to claim 12, wherein the swept volume is a physical space that the robotic linkage could move through in a particular time period based on the velocity of each joint of the plurality of joints.

15. The method according to claim 12, wherein generating the warning of the potential collision includes determining the potential collision based on an overlap between the inferred position of the person and the swept volume of the robotic linkage.

16. The method according to claim 10, wherein analyzing the stereoscopic images includes using an artificial-intelligence learning machine configured to determine the at least one of the type or pose of the human-held tool.

17. The method according to claim 10, wherein inferring the position of the person holding the human-held tool includes:
    accessing information relating to how the human-held tool is typically held during a particular phase of a surgical procedure; and
    inferring the position of the person holding the human-held tool based further on the information relating to how the human-held tool is typically held during the particular phase of the surgical procedure.

18. The method according to claim 17, wherein inferring the position of the person holding the human-held tool includes:
    accessing physical attribute information for the person holding the human-held tool; and
    inferring the position of the person holding the human-held tool based further on the physical attribute information for the person holding the human-held tool,
    wherein the position of the person holding the human-held tool is inferred without using any real-time image of the person holding the human-held tool.

19. A non-transitory computer readable medium including computer executable instructions which, when executed by a controller, cause the controller to perform a method for warning of a potential collision between a person holding a human-held tool and a robotic surgical system having a robotic linkage including a plurality of joints, the method comprising:
    accessing stereoscopic images obtained by an endoscope coupled to a distal portion of the robotic linkage;
    analyzing the stereoscopic images from the endoscope to identify the human-held tool in the stereoscopic images and to estimate at least one of a type or pose of the human-held tool;
    inferring a position of the person holding the human-held tool based on the at least one of the type or pose of the human-held tool;
    determining a spatial relationship between the person and the robotic linkage based on the inferred position of the person; and
    generating a warning of a potential collision between the person and the robotic linkage based on the determined spatial relationship.

20. The non-transitory computer readable medium according to claim 19, wherein the computer executable instructions, when executed by the controller, cause the controller to further perform the method for warning of a potential collision, the method further comprising:
- analyzing the stereoscopic images from the endoscope to identify a robotic tool in the stereoscopic images and to estimate a pose of the robotic tool, the robotic tool being coupled to a distal portion of the robotic linkage; and
- determining a swept volume of the robotic linkage based on the estimated pose of the robotic tool and based on an angle and a velocity of each joint of the plurality of joints,
- wherein generating the warning of the potential collision includes determining the potential collision based on an overlap between the inferred position of the person and the swept volume of the robotic linkage.

* * * * *